US00PP16831P2

(12) United States Plant Patent
de Buck

(10) Patent No.: US PP16,831 P2
(45) Date of Patent: Jul. 18, 2006

(54) ***SEDUM* PLANT NAMED 'POSTMANS PRIDE'**

(50) Latin Name: *Sedum×hybrida*
Varietal Denomination: Postmans Pride

(76) Inventor: José de Buck, Hoge Vorst 14 9968 Bassevelde, Bassevelde (BE)

( * ) Notice: Subject to any disclaimer, the term of this patent is extended or adjusted under 35 U.S.C. 154(b) by 104 days.

(21) Appl. No.: 11/028,791

(22) Filed: Jan. 3, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Sedum* plant named 'Postmans Pride' that is characterized by a compact upright bushy habit and thick succulent very dark brown leaves. In combination these traits set 'Postmans Pride' apart from all other existing varieties of *Sedum* known to the inventor.

2 Drawing Sheets

Genus: *Sedum.*
Species: ×*hybrida.*
Denomination: Postmans Pride.

BACKGROUND OF THE INVENTION

The present invention relates to a new and distinct cultivar of *Sedum* grown as an ornamental for use in container or landscape. The new cultivar is known botanically as *Sedum*× *hybrida* and will be referred to hereinafter by the cultivar name 'Postmans Pride'.

In summer 1999, the inventor carried out at his residence in Bassevelde, Belgium a controlled hybridization between *Sedum* 'Lynda et Rodney' (unpatented) as female parent and *Sedum* 'Purple Emperor' (unpatented) as male parent. Seeds resulting from this cross were collected during fall 1999 and sown immediately. From the resulting seedling population, the inventor removed and isolated 'Postmans Pride' as a single plant which appeared to exhibit distinctly dark brown foliage when compared with either of the parent cultivars or any other variety of *Sedum* known to inventor. The inventor allowed this single plant to grow until spring 2002 in order to determine whether the overall habit of 'Postmans Pride' was commercially acceptable. During 2002, the inventor determined that 'Postmans Pride' exhibits unique and valuable characteristics. The inventor commenced asexual reproduction using internodal stem cuttings with one leaf attached. The inventor has confirmed that all plants thus propagated have remained stable and true to the characteristics of the original seedling selected as 'Postmans Pride'. These initial and subsequent reproductions and determinations were carried out by the inventor at the inventor's nursery in Bassevelde, Belgium.

'Postmans Pride' is characterized by compact, bushy habit, very dark brown succulent leaves, and flowers that are grey-purple and yellow-green in color.

When compared with the female parent plant, *Sedum* 'Lynda et Rodney', 'Postmans Pride' exhibits a more erect plant habit without any tendency to "fall apart" as the plant matures. The inventor has observed this tendency in many dark-leaved selections of *Sedum.*

When compared with the male parent plant, *Sedum* 'Purple Emperor', 'Postmans Pride' exhibits a more consistent and uniform dark brown coloration to the foliage whereas the foliage of 'Purple Emperor' has been observed to "green up" especially in conditions of shade.

Other than the parental cultivars compared above, the only other cultivar of dark-leaved *Sedum* known to the inventor is the *Sedum* plant known as 'Lynda Windsor' (unpatented). Whereas 'Lynda Windsor' achieves a height of 25 cm in one growing season, with average internodes of 4.5 cm, 'Postmans Pride' achieves a height of 20 cm, with average internodes of 2.5 cm.

SUMMARY OF THE INVENTION

The following traits have been repeatedly observed and represent the characteristics of the new *Sedum* cultivar 'Postmans Pride'. These traits in combination distinguish 'Postmans Pride' from all other commercial varieties known to the inventor. 'Postmans Pride' has not been tested under all possible conditions and phenotypic differences may be observed with variations in environmental, climatic and cultural conditions.

1. *Sedum* 'Postmans Pride' exhibits a compact upright and bushy habit.
2. *Sedum* 'Postmans Pride' exhibits very dark brown succulent leaves.
3. *Sedum* 'Postmans Pride' exhibits flowers that are grey-purple and yellow-green in color in late summer and early fall.
4. *Sedum* 'Postmans Pride' exhibits short strong flower stems.
5. *Sedum* 'Postmans Pride' is resistant to mildew.
6. *Sedum* 'Postmans Pride' is hardy to USDA Zone 4.
7. *Sedum* 'Postmans Pride' is propagated using stem cuttings.
8. *Sedum* 'Postmans Pride' is an ornamental suitable for landscape and container.

BRIEF DESCRIPTION OF THE DRAWINGS

The accompanying color drawings illustrate the overall appearance of 'Postmans Pride' showing the colors as true as is reasonably possible to obtain in colored reproductions of this type. Colors in the photographs may differ from the color values cited in the detailed botanical description, which accurately describe the actual colors of the new variety 'Postmans Pride'.

The drawing labeled as FIG. 1 illustrates a close up view of the inflorescence of 'Postmans Pride'.

Figure 1:
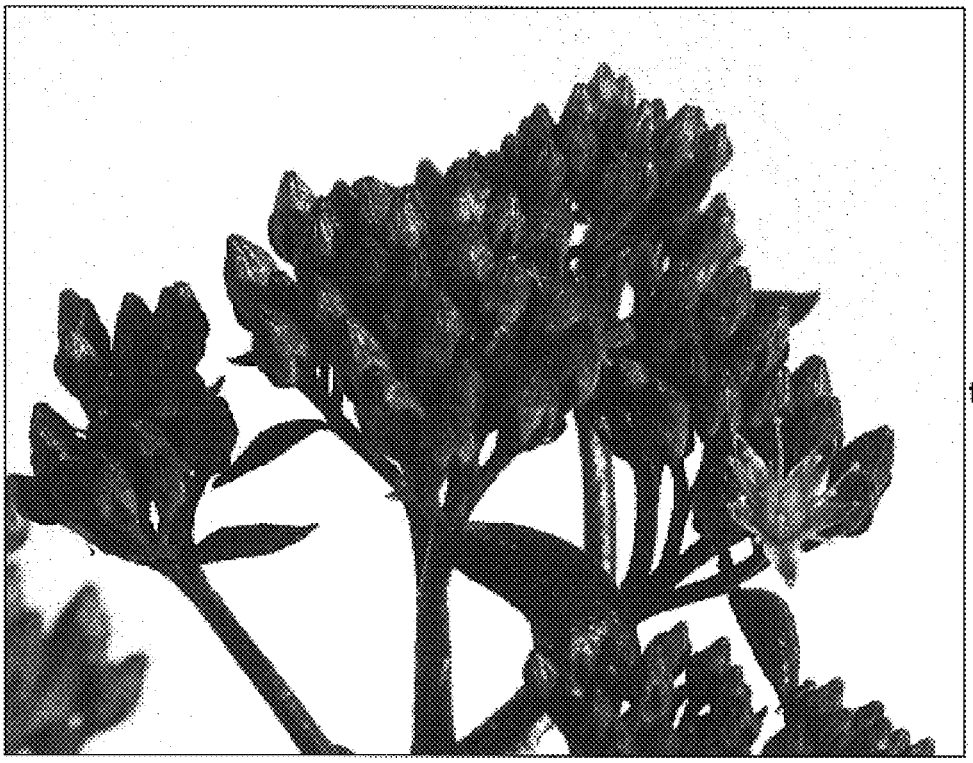
Figure 2:
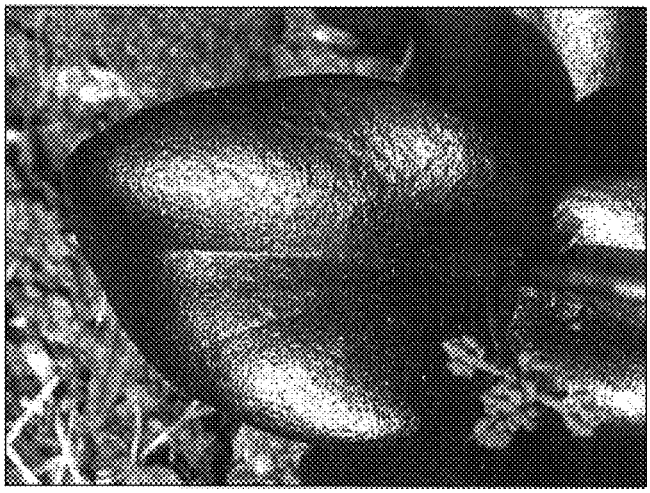

The drawing labeled as FIG. 2 illustrates a close up view of a single leaf of 'Postmans Pride'.

Figure 3:
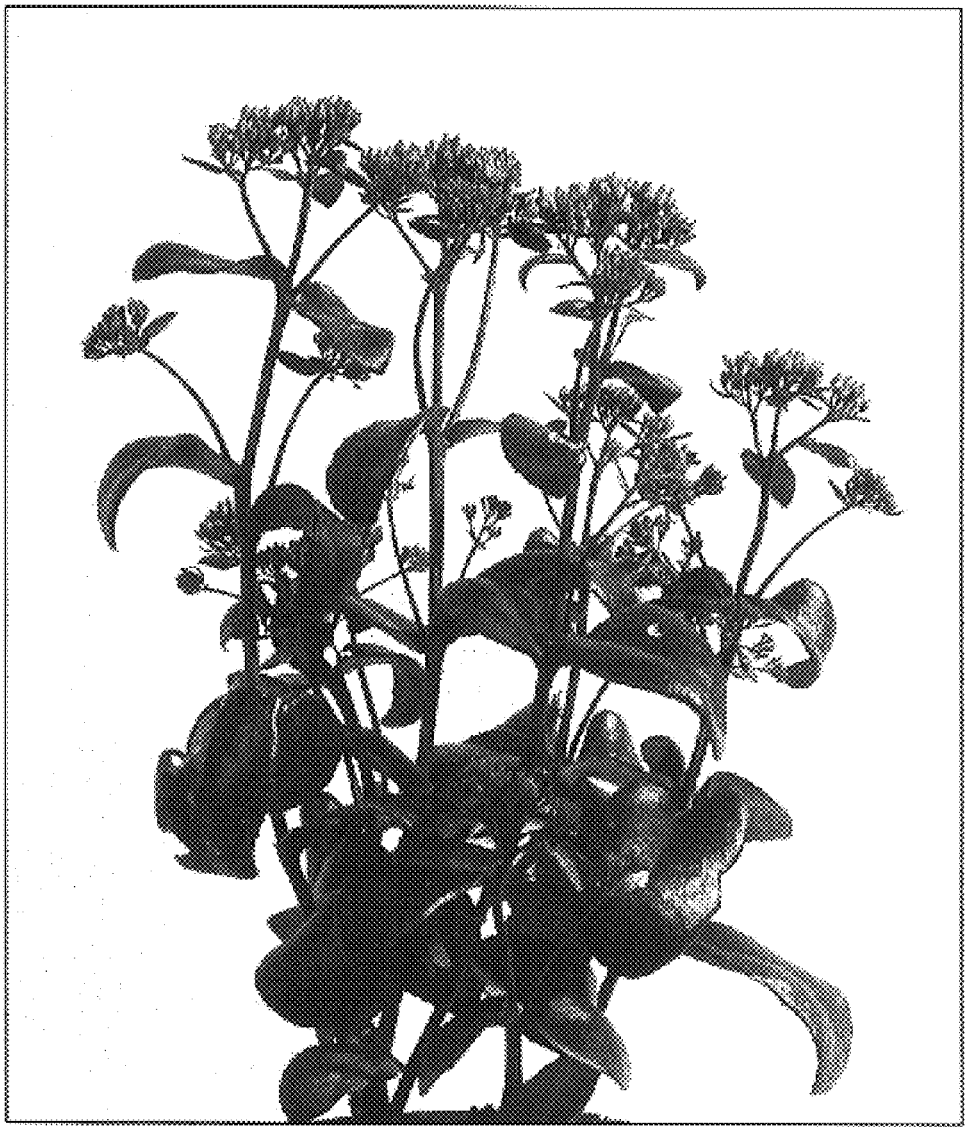

The drawing labeled as FIG. 3 illustrates the entire one year growth of a single plant of 'Postmans Pride'.

The drawings were made in Boskoop, The Netherlands using conventional techniques and although colors may appear different from actual colors due to light reflectance they are as accurate as possible by conventional photography.

BOTANICAL DESCRIPTION OF THE PLANT

The following is a detailed botanical description of 'Postmans Pride' using data collected from a plant of 'Postmans Pride' during its first full year of growth. The plant was started from a cutting in fall 2003 and grown to maturity and seed set in fall 2004. The plant was grown outdoors without protection in Boskoop, The Netherlands. The color determinations are in accordance with the 2001 Royal Horticultural Society Colour Chart of The Royal Horticultural Society, London, England, except where general color terms of ordinary dictionary significance are used. The plant did not receive any chemical treatments. Growing conditions, diseases and pests are similar to that of other *Sedum*. There are no growing problems known to the inventor.

Botanical classification: *Sedum* 'Postmans Pride'.
Species: ×*hybrida*.
Commercial classification: Herbaceous perennial.
Use: Ornamental for landscape and containers.
Cultural requirements: Normal full sunlight to dappled sunlight and well-drained loam soil.
Parentage:
- *Female parent plant.*—*Sedum* 'Lynda et Rodney'.
- *Male parent plant.*—*Sedum* 'Purple Emperor'.

Plant habit: Compact upright bushy habit.
Plant shape: Narrow inverted triangle.
Growth rate: Approximately 5 cm. per month.
Vigor: Moderate.
Hardiness: Hardy to USDA Zone 4.
Crop time: If grown from cuttings taken in the fall, an average of 8–9 months is required to produce a finished flowering plant in a 1 liter container out of doors. Plants may be started from cuttings taken in the spring in which case flowering takes place in approximately five months on plants which are less well-branched.
Root system: Fine and fibrous.
Propagation: Propagation is accomplished using stem cuttings.
Plant dimensions: 25 cm. in height and 17 cm. in width.
Stem:
- *Branching habit.*—Basal branching of main stems and lateral branches.
- *Shape.*—Cylindrical.
- *Number of lateral branches.*—Average of 6 per main stem.
- *Stem color.*—N186C.
- *Stem length.*—Average of 15 cm.
- *Stem diameter.*—Average of 2.5 mm.
- *Stem surface.*—Glabrous and shiny.
- *Internode length.*—Average of 3.8 cm.
- *Texture.*—Succulent.
- *Strength.*—Moderate.
- *Pubescence.*—None.
- *Special requirements.*—None, but pinching will improve branching.

Foliage:
- *Type.*—Evergreen.
- *Arrangement.*—Opposite.
- *Single or compound leaf.*—Single.
- *Number of leaves per lateral branch.*—Average of 6 (3 pairs).
- *Shape.*—Ovate, carinate and curved.
- *Division.*—Simple.
- *Margins.*—Very sparsely dentate, average of 2 teeth per cm.
- *Apex.*—Rounded.
- *Base.*—Obtuse.
- *Vein pattern.*—Pinnate but only main vein is visible.
- *Vein color* (*adaxial surfaces of young and mature leaves*).—Towards leaf base, 186A; elsewhere same as leaf surface color.
- *Vein color* (*abaxial surfaces of young and mature leaves*).—Between 147A and 147B.
- *Leaf arrangement.*—Average of 5.8 cm.
- *Leaf thickness.*—1.5 mm.
- *Leaf with.*—Average of 3.4 cm.
- *Young leaf color* (*adaxial surface*).—Between 186A and 200A.
- *Young leaf color* (*abaxial surface*).—186C; tending to yellow-green, between 146A and 146B, towards base.
- *Mature leaf color* (*adaxial surface*).—Between N186D and 200A.
- *Mature leaf color* (*abaxial surface*).—N186C, tending to 147A towards base.
- *Texture.*—Slightly glossy, succulent.
- *Young leaf surfaces* (*abaxial and adaxial*).—Dull.
- *Mature leaf surfaces* (*abaxial and adaxial*).—Dull.
- *Pubescence.*—None.
- *Attachment.*—Sessile.
- *Durability to stress.*—High.
- *Stipules.*—None.
- *Spines.*—None.
- *Fragrance.*—None.

Flowers:
- *Flower arrangement.*—Terminal.
- *Inflorescence type.*—Compound cyme.
- *Inflorescence height.*—Average 3.2 cm.
- *Inflorescence width.*—Average 4.2 cm.
- *Quantity of flowers per inflorescence.*—Average of 45 per inflorescence.
- *Flower shape.*—Rotate.
- *Flowering months.*—August and September.
- *Quantity of flowers per lateral stem.*—Average of approximately 100 per lateral stem.
- *Quantity of buds per lateral stem.*—Average of approximately 100 per lateral stem.
- *Quantity of flowers and buds per plant.*—Average of approximately 600 per plant.

*Natural flowering season.*—Late summer to early fall.
*Flower response time.*—Approximately 9 months.
*Proportion of flowers open at any one time.*—Approximately 60% of the flowers are open at any one time.
*Fragrance.*—None.
*Bud dimensions.*—4 mm. in length and 2 mm. in diameter.
*Bud shape.*—Ovate to elliptic.
*Rate of opening.*—Individual flowers open in approximately 5 days.
*Bud color.*—146A towards base; darkens to 187A and N187A towards apex.
*Flower aspect.*—Upright to slightly outward.
*Flower shape.*—Rotate.
*Flower dimensions.*—8 mm. in diameter and 5 mm. in height.
*Flower longevity on the plant.*—Approximately 14 days.
*Flower longevity off the plant.*—Approximately 10 days.
*Persistent or self-cleaning.*—Persistent.
*Petal shape.*—Narrow, ovate.
*Petal texture.*—Dull.
*Petal surface.*—Glabrous.
*Petal arrangement.*—Rotate.
*Number of petals.*—Five in number.
*Fused or unfused.*—Basally fused.
*Petal margin.*—Entire.
*Petal apex.*—Acute.
*Petal dimensions.*—5 mm. in length and 1.5 mm. in width.
*Petal color when opening* (*both surfaces*).—Colors 146C and 146D are individually present on an individual petal. Surfaces heavily dotted, dots 187C and 187D. Color towards base lighter, 147D.
*Petal color fully opened* (*both surfaces*).—Colors 146B and 146C are individually present on an individual petal. Surfaces heavily dotted, dots 187C. Color towards base lighter, 147D.
*Peduncle dimensions.*—3.7 cm. in length and 2 mm. in diameter.
*Peduncle surface.*—Glabrous.
*Peduncle angle.*—Average angle of 25° to the vertical (except central cyme which is straight and upright).
*Peduncle strength.*—Moderately strong.
*Peduncle color.*—Slightly darker than N186C.
*Pedicels.*—Present.
*Pedicel dimensions.*—7 mm. in length and 0.8 mm. in width.
*Pedicel angle.*—Average 30° to the vertical (varies between 0° to 45°).
*Pedicel strength.*—Moderately strong.
*Pedicel color.*—N186C with slight shading of 147A.
*Pedicel surface.*—Glabrous.
*Calyx shape.*—Campanulate.
*Calyx dimensions.*—2.5 mm. in length and 3 mm. in diameter.
*Sepal color* (*both surfaces, immature and mature*).—147A, lighter at base, 146A.
*Number of sepals.*—Five in number.
*Sepal arrangement.*—Rotate, campanulate.
*Sepal surfaces* (*adaxial and abaxial surfaces*).—Dull, smooth.
*Sepal shape.*—Narrow ovate.
*Fused or unfused.*—Sepals basally fused.
*Sepal margin.*—Entire.
*Sepal apex.*—Acute.
*Sepal base.*—Broad, cuneate (fused).
*Sepal dimensions.*—2.5 mm. in length and 0.8 mm. in width.

Reproductive organs:
*Stamens.*—10 in number.
*Arrangement.*—5 stamens arranged in base of petals, 5 stamens free.
*Stamen length.*—2.25 mm.
*Stamen color.*—184C.
*Filament length.*—4 mm.
*Filament color.*—49D.
*Anther shape.*—Flattened oblong.
*Anther length.*—0.5 mm.
*Anther color.*—22A.
*Amount of pollen.*—Small amount.
*Pollen color.*—14A.
*Pistil.*—5 in number.
*Pistil length.*—4 mm.
*Stigma shape.*—Acute.
*Stigma color.*—186C.
*Style length.*—3.5 mm.
*Style color.*—N144A.
*Ovary color.*—N144A.

Seed production:
*Quantity of seed.*—Average of 5 per ovary.
*Seed length.*—1 mm. in length.
*Seed diameter.*—0.5 mm. in diameter.
*Seed color.*—199A.
*Quantity of fruit per lateral branch.*—Average of 45 fruit.
*Fruit length.*—4 mm. in length.
*Fruit diameter.*—2 mm. in diameter.
*Fruit color.*—Both individual colors 177A and 146A are present on an individual fruit.
*Fruit texture.*—Dull and glabrous.

What is claimed:

1. A new and distinct cultivar of *Sedum* plant named 'Postmans Pride' as described and illustrated herein.

* * * * *